(12) United States Patent
Krissmann et al.

(10) Patent No.: US 7,368,621 B2
(45) Date of Patent: May 6, 2008

(54) METHOD FOR PRODUCING 1-OCTENE FROM CRACK-$C_4$

(75) Inventors: Joerg Krissmann, Kleinostheim (DE); Dirk Roettger, Recklinghausen (DE); Cornelia Borgmann, Recklinghausen (DE); Kerstin Kaemper, Waltron (DE); Franz Nierlich, Marl (DE); Alfred Kaizik, Marl (DE); Udo Knippenberg, Marl (DE); Rainer Malzkorn, Mobile, AL (US)

(73) Assignee: OXENO Olefinchemie GmbH, Marl (DE)

( * ) Notice: Subject to any disclaimer, the term of this patent is extended or adjusted under 35 U.S.C. 154(b) by 60 days.

(21) Appl. No.: 10/562,454

(22) PCT Filed: May 6, 2004

(86) PCT No.: PCT/EP2004/050722

§ 371 (c)(1),
(2), (4) Date: Aug. 18, 2006

(87) PCT Pub. No.: WO2005/000772

PCT Pub. Date: Jan. 6, 2005

(65) Prior Publication Data

US 2006/0281959 A1     Dec. 14, 2006

(30) Foreign Application Priority Data

Jun. 27, 2003   (DE) ................ 103 29 042

(51) Int. Cl.
*C07C 1/207* (2006.01)
(52) U.S. Cl. ............... 585/328; 585/327; 585/324; 585/639

(58) Field of Classification Search ................ 585/328, 585/327, 324, 639
See application file for complete search history.

(56) References Cited

U.S. PATENT DOCUMENTS

| | | |
|---|---|---|
| 5,177,282 A | 1/1993 | Nierlich et al. |
| 6,015,928 A | 1/2000 | Gubishc et al. |
| 6,184,424 B1 | 2/2001 | Bueschken et al. |
| 6,239,318 B1 | 5/2001 | Schuler et al. |
| 6,331,657 B1 | 12/2001 | Kaizik et al. |
| 6,403,836 B2 | 6/2002 | Kaizik et al. |
| 6,407,295 B1 | 6/2002 | Kaizik et al. |

(Continued)

FOREIGN PATENT DOCUMENTS

DE    101 49 348    4/2003

(Continued)

OTHER PUBLICATIONS

U.S. Appl. No. 10/538,475, filed Jun. 7, 2005, Kaizik, et al.

(Continued)

*Primary Examiner*—Thuan Dinh Dang
(74) *Attorney, Agent, or Firm*—Oblon, Spivak, McClelland, Maier & Neustadt, P.C.

(57) ABSTRACT

The invention relates to a process for preparing 1-octene from a $C_4$ fraction from a cracker by telomerization of the 1,3-butadiene present in the $C_4$ fraction from a cracker by means of methanol in the presence of a catalyst, hydrogenation of the telomer obtained in this way, dissociation of the hydrogenated telomer and work-up of the resulting dissociation product to give pure 1-octene.

16 Claims, 8 Drawing Sheets

U.S. PATENT DOCUMENTS

| | | |
|---|---|---|
| 6,433,230 B1 | 8/2002 | Bueschken et al. |
| 6,482,992 B2 | 11/2002 | Scholz et al. |
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Rottger et al. |
| 6,603,047 B2 | 8/2003 | Wiese et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,002,053 B2 | 2/2006 | Nierlich et al. |
| 7,009,068 B2 | 3/2006 | Schmutzler et al. |
| 7,109,346 B2 | 9/2006 | Beller et al. |
| 7,161,053 B2 | 1/2007 | Beckmann et al. |
| 2004/0059170 A1 | 3/2004 | Rottger et al. |
| 2004/0236133 A1 | 11/2004 | Selent et al. |
| 2004/0238787 A1 | 12/2004 | Wiese et al. |
| 2004/0242947 A1 | 12/2004 | Beller et al. |
| 2005/0038273 A1 | 2/2005 | Rottger et al. |
| 2005/0043279 A1 | 2/2005 | Selent et al. |
| 2005/0065387 A1 | 3/2005 | Beller et al. |
| 2005/0182277 A1 | 8/2005 | Totsch et al. |
| 2005/0209489 A1 | 9/2005 | Moller et al. |
| 2005/0234270 A1 | 10/2005 | Kaizik et al. |
| 2005/0240039 A1 | 10/2005 | Rottger et al. |
| 2005/0256281 A1 | 11/2005 | Grund et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0183936 A1 | 8/2006 | Grass et al. |
| 2006/0241324 A1 | 10/2006 | Moeller et al. |

FOREIGN PATENT DOCUMENTS

| | | |
|---|---|---|
| WO | 92/10450 | 6/1992 |

OTHER PUBLICATIONS

U.S. Appl. No. 10/538,359, filed Jun. 13, 2005, Roettger, et al.
U.S. Appl. No. 10/576,302, filed Apr. 19, 2006, Kaizik, et al.
U.S. Appl. No. 11/574,060, filed Feb. 22, 2007, Borgmann, et al.
U.S. Appl. No. 11/574,018, filed Feb. 21, 2007, Borgmann, et al.
U.S. Appl. No. 11/721,978, filed Jun. 16, 2007, Beller, et al.
U.S. Appl. No. 11/574,063, filed Feb. 22, 2007, Neirlich, et al.

METHOD FOR PRODUCING 1-OCTENE FROM CRACK-C$_4$

The invention relates to a process for preparing 1-octene from a C$_4$ fraction from a cracker telomerization of the 1,3-butadiene present in the C$_4$ fraction from a cracker by means of methanol in the presence of a catalyst, hydrogenation of the telomer obtained in this way, dissociation of the hydrogenated telomer and work-up of the resulting dissociation product to give pure 1-octene.

1-octene is used in large quantities in the production of various chemical products. For example, surface-active substances, plasticizers, lubricants and polymers are produced from 1-octene. Another large, field of application is its use as comonomer in polymers, especially in polyethylene.

Virtually all processes which are at present utilized commercially for the production of 1-octene are based on ethene as raw material. Ethene is oligomerized to give a range of α-olefins as main products. With appropriate choice of catalyst and process conditions, the amount of 1-octene in the product can be optimized and is then about 25%. Apart from these processes, by means of which most 1-octene is produced, the isolation of 1-octene from the product mixture from the Fischer-Tropsch reaction has attained some importance.

Apart from ethene-based processes, processes which use 1,3-butadiene as raw material are also known from the literature. However, 1-octene is not obtainable directly, for example by means of a dimerization, from butadiene, but is obtained after a plurality of process steps. Thus, WO 92/10450 describes a process in which 1,3-butadiene is reacted with, preferably, methanol or ethanol to form a 2,7-octadienyl ether which, after hydrogenation to form the octyl ether, is dissociated to give 1-octene. An analogous route is employed in EP-A-0 440 995, but the reaction in the first step is with a carboxylic acid. Both processes involve a first process step which is generally referred to as telomerization. In telomerization, a telogen (in EP-A-0 440 995 the carboxylic acid) is generally reacted with a taxogen (1,3-butadiene, 2 equivalents) to form a telomer.

Recent process variants are described, for example, in DE 10 10 5751, DE 10 12 8144, DE 10 14 9348, DE 10 14 9347 and DE 10 22 9290.

These processes employ the abovementioned steps of telomerization, hydrogenation and subsequent dissociation and produce not only the desired target product 1-octene but also by-products which have to be separated off from the target product. Since 1-octene is frequently used as a comonomer, the preparation of highly-pure 1-octene is desirable. The present invention achieves this object.

To clarify the nontrival separation problem, Table 1 below shows the typical composition of a dissociation product obtained by the abovementioned processes; FIG. 1 shows the associated boiling points. It can easily be seen that 1-octene cannot: be separated off in the desired purities by simple distillation of the dissociation product.

TABLE 1

Example of a composition of a dissociation product

| Component | % by weight |
|---|---|
| Dimethyl ether | 5.90 |
| Methanol | 1.50 |
| Water | 2.30 |
| C1-C7-hydrocarbons | 0.02 |
| 1-octene | 33.90 |

TABLE 1-continued

Example of a composition of a dissociation product

| Component | % by weight |
|---|---|
| 2-octenes | 1.70 |
| 3/4-octenes | 0.63 |
| 1-octanol | 2.76 |
| 2-octanol | 0.26 |
| 2-octanone | 0.15 |
| Other C8-hydrocarbons | 0.24 |
| C9-hydrocarbons | 1.36 |
| >C9-hydrocarbons | 0.53 |
| 1-methoxyoctane | 46.00 |
| Dioctyl ether | 1.70 |
| Others | 1.05 |

It has now surprisingly been found that despite this complex composition, 1-octene can be prepared in satisfactory purity from a C$_4$ fraction from a cracker by means of a particular distillation process, if appropriate with an upstream water scrub.

The present invention accordingly provides a process for preparing 1-octene by
a) catalytic reaction of a butadiene-containing stream with methanol to give a stream comprising at least 1-methoxy-2,7-octadiene,
b) catalytic hydrogenation of the 1-methoxy-2,7-octadiene-containing stream to give a stream comprising at least 1-methoxyoctane,
c) catalytic dissociation of at least part of the 1-methoxyoctane to give a dissociation product comprising at least water and 1-octene, wherein
d) the dissociation product from c) is separated by distillation into a gaseous low-boiling fraction comprising at least 1-octene and water and a liquid high-boiling fraction comprising at least 1-octene and 1-methoxyoctane,
e) the low-boiling fraction is completely or partially condensed and separated into an aqueous phase and a 1-octene-containing, nonpolar phase,
f) the nonpolar phase from e) is recirculated to step d) and
g) the high-boiling fraction from d) is separated into a 1-octene-containing fraction and a 1-methoxyoctane-containing fraction.

Figure 1:
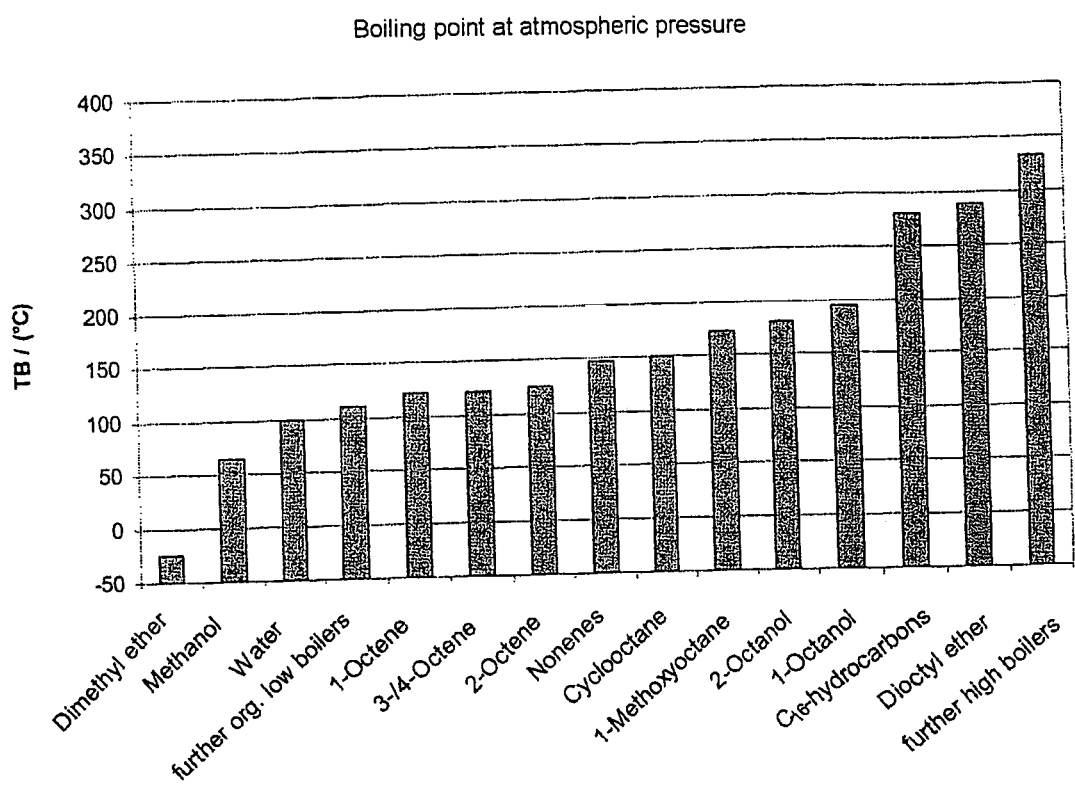
FIG. 1 shows the boiling points of various relevant materials at atmospheric pressures.

Process steps a) to c) of the process of the invention do not differ from the prior art and are described, for example, in the abovementioned patent documents, in particular in DE 10 10 5751, DE 10 12 8144, DE 10 14 9348, DE 10 14 9347 and DE 10 22 9290. These processes are hereby expressly incorporated by reference.

In process step a) of the process of the invention, which comprises the telomerization, it is possible to use butadiene-containing streams, e.g. $C_4$ streams from a cracker. Typical butadiene concentrations in these streams range from 20 to 70% of 1,3-butadiene. The remaining components n-butane, isobutane, 1-butene, 2-butene and isobutene do not interfere or interfere only insignificantly in the reaction in the telomerization step. However, other dienes, e.g. allenes, or acetylenes, in particular vinylacetyle, are advantageously removed from distillation, extraction or selective hydrogenation.

Preferred telomerization catalysts are nickel, rhodium, palladium or platinum catalysts, for example those having phosphorus-containing ligands such as phosphines (e.g. triphenylphosphine), phosphites (e.g. trimethyl phosphite), phosphonites or phosphinites (e.g. diphenylphenoxyphosphine). Preference is given to using catalysts of this type having carbene ligands. The use of a base, e.g. a metal hydroxide, alkoxide or phenoxide, or a solvent, e.g. an inert aliphatic hydrocarbon, in this process step is optional.

The telomerization reaction is preferably carried out at from 10° C. to 200° C. and a reaction pressure of from 1 to 300 bar.

As telogen, use is made exclusively of methanol in the process of the invention. From 0.1 mol to 4 mol of 1,3-butadiene can be used per mole of methanol.

The 1-methoxy-2,7-octadiene obtained in step a) is hydrogenated in step b).

The hydrogenation can be carried out as a liquid-phase and/or gas-phase hydrogenation or in a combination of these techniques and can be carried out in one or more steps, for example in a prehydrogenation and a final hydrogenation.

The hydrogenation can be carried out continuously or batchwise. As reactors, it is possible to use the known standard reactors for hydrogenations, for example trickle-bed reactors. The heat of reaction evolved in the reaction is removed by known methods, for example by means of internal or external coolers. Specifically, this can mean the use of shell-and-tube reactors, cooling fingers, cooling coils or plates or cooling of a recycle stream (reactors with circulation, recycling).

The hydrogenation is carried out in the presence of a catalyst. It is possible to use either homogeneous or heterogeneous catalysts. For example, the catalyst can comprise at least one element of groups 8-10 of the Periodic Table of the Elements. Optionally, further transition metals can also be used as catalysts for this hydrogenation, in particular copper and/or chromium and/or at least one further metal of groups 8-10 of the Periodic Table of the Elements.

In the case of heterogeneous catalysts, the abovementioned metals can be modified with other metals or moderators. Thus, for example, the activity and selectivity of heterogeneous palladium catalysts are often modified by addition of sulfur or carbon monoxide. Copper catalysts often have a proportion of chromium added to them.

The use of supported catalysts is generally advantageous since relatively small amounts of metal are needed and the properties of the catalyst can additionally be influenced via the nature of the support. Support materials which have been found to be useful are, for example, activated carbon, aluminum oxide, silicon dioxide, silicon-aluminum oxide, barium carbonate, barium sulfate and kieselguhr.

The hydrogenations are carried out at temperatures of from 0 to 400° C., preferably from 20 to 200° C. The pressure is from 0.01 to 300 bar, preferably from 0.1 to 125 bar, particularly preferably from 1 to 64 bar.

The hydrogenation of the 1-methoxy-2,7-octadiene to 1-methoxyoctane in the liquid phase, regardless of whether it is homogeneously or heterogeneously catalyzed, can be carried out in the presence or absence of further components. Possible further components are starting materials and by-products from step a) which have not yet been separated off and any solvents which may have been added. Starting materials for step a) which are still present can be, for example, methanol or C4-hydrocarbons, while typical by-products of the telomerization reaction are 3-methoxy-1,7-octadiene, 1,3,7-octatrienes, 1,7-octadiene, 1,6-octadienes and vinylcyclohexene.

Components from step a) which are present in the hydrogenation may themselves be completely or partially hydrogenated. Thus, complete hydrogenation forms, for example, 3-methoxyoctane, from 3-methoxy-1,7-octadiene, octaine from 1,3,7-octatriene, 1,7-octadiene and 1,6-octadiene, ethylcyclohexane from vinylcyclohexene, and butane from 1,3-butadiene and n-butenes.

Examples of solvents which can additionally be added in the hydrogenation are aliphatic, cycloaliphatic and aromatic hydrocarbons (octane, ethylcyclohexane), alcohols (methanol) and ethers (dimethyl ether, methyl octyl ether, 3-methoxyoctane). The solvents are used either alone or as mixtures of various solvents. The hydrogenation is preferably carried out without addition of additional solvents.

In the case of hydrogenations in the gas phase, other gases can be present in addition to hydrogen and substrate. For example, nitrogen and/or argon and also alkanes which are gaseous under the hydrogenation conditions, for example methane, propane or butane, can be added or be present in the hydrogenation gas.

The hydrogenation in step b) of the process of the invention can be carried out continuously, semicontinuously or discontinuously (batchwise). Preference is given to a continuous process.

In step b) of the process of the invention, virtually complete reaction of the 1-methoxy-2,7-octadiene is preferably sought. The conversion is preferably greater than 98%, in particular greater than 99.5%.

In a preferred embodiment of the process of the invention, the hydrogenation is carried out in the liquid phase over a heterogeneous supported palladium catalyst which preferably contains from 0.01 to 5 percent by weight (% by weight) of palladium. The pressure in this hydrogenation is preferably from 1 to 64 bar and the temperature is from 10 to 140° C. The hydrogenation is carried out in two stages, with both stages optionally being able to be operated with product recirculation.

As raw material for step c) of the process of the invention, preference is given to using 1-methoxyoctane of high purity. The 1-methoxyoctane content is preferably >99% by weight. To achieve this purity, it is advantageous to separate off other components. This can be achieved, for example, by distillation after the hydrogenation, before the hydrogenation or both before and after the hydrogenation in the process. $C_4$-hydrocarbons present in the reaction mixture from the telomerization, step a), are preferably separated off prior to the hydrogenation. Other components such as methanol, $C_8$-hydrocarbons or 3-methoxy-1,7-octadiene can be removed before or after (then generally in saturated form) the hydrogenation.

In a preferred embodiment of the process of the invention, step a) comprises a process step k) in which $C_4$-hydrocarbons are separated off by distillation after the catalytic reaction. The remaining stream, which has a $C_4$-hydrocarbon content of less than 5% by weight, is passed to step b). In this separation, part of the methanol present in the stream is also removed as azeotrope with the $C_4$-hydrocarbons (about 3-6% by weight of methanol in the $C_4$ stream). The remaining mixture comprises mainly 1-methoxy-2,7-octadiene and methanol in a total amount of >80% by weight. Secondary components are, apart from any residual amounts of $C_4$-hydrocarbons present, mainly 3-methoxy-1,7-octadiene, 1,3,7-octatriene, 1,7-octadiene, 1,6-octadiene and vinylcyclohexene. This mixture is passed to a hydrogenation step b) in which, in addition to the hydrogenation of 1-methoxy-2,7-octadiene to 1-methoxyoctane, the secondary components are converted into 3-methoxyoctane, n-octane, ethylcyclohexane and possibly ethylcyclohexene.

The reaction mixture (stream) from the hydrogenation in step b) can, in a preferred variant, subsequently be purified by distillation in a process step 1) in which a low-boiling fraction comprising methanol, 3-methoxyoctane and $C_8$-hydrocarbons, in particular n-octane, ethylcyclohexane and ethylcyclohexene, is separated off. If $C_4$-hydrocarbons were present in the feed to the hydrogenation, these are also hydrogenated and are obtained together with the low-boiling fraction, possibly as an offgas stream, at the top of the distillation column. In addition to the low-boiling fraction, a high-boiling fraction comprising 1-methoxyoctane is obtained and is passed to step c).

An advantage of this work-up is, inter alia, that the number of components occurring as by-products is reduced by the hydrogenation, which further simplifies a further work-up of this stream.

The $C_4$-hydrocarbon fraction obtained when the C4-hydrocarbons are separated off in process step k), which can have a methanol content of from about 3 to 6%, can advantageously be passed to a selective hydrogenation, process step m), in which residual 1,3-butadiene is converted into 1-butene and 2-butenes. Such hydrogenations are prior art. The hydrogenation is preferably carried out in the liquid phase over heterogeneous supported palladium catalysts.

The reaction mixture from this hydrogenation (process step m) can then, for example, be passed to an etherification in which the methanol is reacted with the isobutene present in the $C_4$ stream to form methyl tert-butyl ether. This reaction, too, is carried out by methods known in industry, usually in the presence of ion exchangers as catalysts. To achieve complete conversion of the isobutene, it may be necessary to add additional methanol.

As an alternative, the reaction mixture from the hydrogenation (process step m) can be scrubbed with water in a process step n) to remove the methanol. This gives an essentially methanol-free organic phase which corresponds to commercial raffinate I and an aqueous phase. The aqueous, methanol-containing phase is preferably separated by distillation into methanol and water, and the water is wholly or partly returned to the extraction (process step n) while the methanol is wholly or partly recirculated to step a) of the process of the invention. To produce this raffinate I it is also possible for the extraction with water (process step n) to be carried out first and a selective hydrogenation (process step m) of the dienes of the $C_4$ stream to be carried out subsequently.

The raffinate I can be processed further in accordance with known methods, for example to produce tert-butyl alcohol, diisobutene (or isooctane), methyl tert-butyl ether, 1-butene or $C_4$-dimers and oligomers as described, for example, in DE 101 02 082, DE 25 38 036, DE 39 14 817, DE 103 02 457 or DE 103 06 214.

In process step c), the 1-methoxyoctane obtained in this way is dissociated over a catalyst to give methanol and 1-octene. By-products which may also be formed here are dimethyl ether (DME) and water.

The dissociation reaction is carried out in the presence of heterogeneous catalysts. Preference is given to using catalysts such as aluminum oxide, silica, silicates, basic catalysts, aluminum-containing silicas, clay minerals or zeolites. As basic catalysts, preference is given to using catalysts which are described in the German patent application number DE 102 57 499. The dissociation reaction is carried out at a temperature of from 100 to 800° C., preferably from 150 to 600° C., particularly preferably from 250 to 500° C. The pressure used here is from 0.05 to 300 bar, preferably from 1 to 25 bar, particularly preferably from 1 to 5 bar.

The dissociation product obtained after steps a) to c) can be processed further in a number of process variants. In the simplest case, the dissociation product from c) can be separated directly by distillation into a gaseous low-boiling fraction comprising at least 1-octene and water and a liquid high-boiling fraction comprising at least 1-octene and 1-methoxyoctane (process step d)).

However, since DME and water are frequently present in the dissociation product, part, preferably the major part, of the DME is preferably separated off first from the dissociation product by distillation. This can be carried out in a step d1) in which the dissociation product from c) is separated by distillation into a low-boiling fraction comprising at least DME and a high-boiling fraction which is passed to step d). If methanol is present in the high-boiling fraction from d1), it can be advantageous to wash this fraction with water to give, after phase separation (e.g. in a phase separator), a methanol-containing aqueous stream and a nonpolar stream which is passed to step d).

In another embodiment of the process of the invention, the methanol-containing dissociation product from step c) is firstly washed with water in a process step d2), e.g. by means of a decanter or a countercurrent extraction, to give a methanol-containing aqueous stream and a nonpolar stream. All or part of the nonpolar stream can then be passed to step d). In this process step, the methanol formed in the dissociation is largely separated off. The extraction is preferably carried out at a temperature of from 10 to 75° C. and a mass ratio of the stream to be purified to water of from 1:10 to 10:1.

If DME is also present in the nonpolar stream from process step d2), this stream can be separated by distillation into a low-boiling fraction comprising at least DME and a high-boiling fraction which is passed to step d). The removal of the DME by distillation can, for example, be carried out by feeding the nonpolar stream into step d1). If no step d1) is employed, DME can be taken at the top of the column of step d), preferably as a gaseous offgas stream (only partial condensation of the gaseous low-boiling fraction.

Steps d), d1) and d2) can be connected so that the streams or substreams pass one or more times through all or part of the steps. Particularly effective removal of DME and methanol can be achieved in this way.

The dimethyl ether (DME) separated off in steps d), d1) or d2) can, for example, be used as heating gas (thermal utilization), as raw material for chemical processes (for example olefin syntheses) or fuel cells or as blowing gas. The purity requirements for the DME differ depending on the application. In a preferred embodiment of step d1), the DME is obtained in a purity of >99%, in particular >99.9%, very particularly preferably >99.99%, and is used as blowing gas.

The separation steps d), e), f) are preferably carried out in a distillation column which is operated at a pressure of from 0.5 to 10 bar, preferably at a pressure of from 2 to 4 bar, in an overhead condenser at an operating temperature of from about 15 to 75° C. and in a phase separation vessel (decanter).

In step e), the low boilers obtained in step d) are completely or partially condensed in the overhead condenser, the liquid phase is transferred to the decanter and separated into a polar phase and a nonpolar phase in the decanter. A gas phase (e.g. DME) is optionally obtained in the condensation, and this is taken off (in the case of partial condensation). If the condensate is not made up of two phases, the addition of an appropriate amount of water in the distillation step d) or in the decanter is advantageous.

The organic (nonpolar) phase from the decanter is returned in its entirety to the column, while the aqueous phase is used further elsewhere.

This step avoids losses of 1-octene which would otherwise occur as a result of the formation of the minimum azeotrope of water and 1-octene.

The high-boiling fraction obtained from the distillation in step d) is a mixture comprising the octene isomers, 1-methoxyoctane and small amounts of secondary components such as 1-octanol, $C_{9+}$-hydrocarbons (hydrocarbons having 9 or more carbon atoms). This mixture is fractionated in process step g) of the process of the invention to give a 1-octene-containing fraction and a 1-methoxyoctane-containing fraction. This distillation is carried out at from 50 to 250° C. and a pressure of from 0.1 to 5 bar.

The 1-octene stream obtained in this way can further comprise other octene isomers and nonene isomers and is satisfactory for many applications in this form. The 1-octene concentration in this stream is from 80 to 98% by weight.

If 1-octene is to be prepared in a purity of over 90% by weight, the 1-octene-containing fraction from g) is advantageously separated in a process step h) into a fraction comprising at least 1-octene and a fraction comprising at least $C_8$-and/or $C_9$-olefins. The unwanted octene isomers or the nonenes are preferably separated off at a temperature of from 50 to 250° C. and a pressure of from 0.1 to 5 bar. The target product 1-octene is obtained here as overhead product in a purity of >90% by mass, preferably >95% by weight, particularly preferably 98.5% by weight. The $C_8$-, $C_9$-hydrocarbons separated off as bottom product can, for example, be used as raw materials in the production of plasticizer alcohols.

The 1-methoxyoctane which has not been converted in the dissociation process c) is obtained together with further high boilers as bottom product in the distillation of process step g). This stream is preferably recirculated to the catalytic dissociation c), with the abovementioned high boilers, for example dioctyl ether and other hydrocarbons, being most simply removed from the system via a small bleed stream. Another option is to separate the 1-methoxyoctane-containing fraction from g) into a low-boiling fraction comprising at least 1-methoxyoctane and a high-boiling fraction comprising at least dioctyl ether (process step i). This distillation is preferably carried out at a temperature of from 100 to 300° C. at a pressure of from 0.1 to 2.5 bar. The 1-methoxyoctane obtained in this way has a purity of from 90 to 100% by weight and is advantageously recirculated to the dissociation reaction c). The high-boiling fraction comprising dioctyl ether from step i) can be passed to thermal utilization or another use, for example for producing synthesis gas.

If methanol-containing, aqueous streams are obtained in the process of the invention, for example in process steps d1), d2), e) and n), e.g. as a result of an extraction, it can be advantageous for these to be worked up in a process step o) so that methanol and/or water are separated off. All or part of the methanol can be recirculated to the telomerization in step a). This separation is preferably achieved by distillation. If a second, organic phase is present in addition to the water/methanol phase, this is preferably separated off prior to the distillation and the aqueous phase is separated by distillation into a methanol-containing low-boiling fraction and a water-containing high-boiling fraction.

The work-up of the methanol-containing, aqueous streams as are obtained, for example, from step d2) can also be carried out together with further streams of the process. Further streams which are suitable for this purpose are, in particular, the aqueous phase from step e), the methanol-containing low-boiling fraction from process step 1) and the aqueous, methanol-containing phase from process step n).

It is particularly advantageous to work up the streams so that only one methanol/water mixture is obtained and is separated again into methanol and water in a central unit. The water can then be recirculated to the extractions present in the process of the invention and methanol can be returned to step a) of the process of the invention. Examples of joint work-up of methanol-containing streams are discussed in the process variants described below.

One process variant is explained below with the aid of FIG. 2: stream (1) denotes the dissociation product which is obtained from process step c) and typically has the composition indicated in Table 1. In the scrubbing step (2) (process step d2)), the dissociation product is scrubbed with water (3) to give an aqueous solution (4). The nonpolar stream (5) is subsequently separated in the distillation column (6) (process step d)) into a low-boiling fraction (7) comprising mostly DME, water and octenes and the high-boiling fraction (13) comprising the major part of the 1-octene, high boilers and 1-methoxyoctane. The low-boiling fraction (7) is partially condensed (8) with discharge of a gaseous stream (9) (DME) and separated in the decanter (10) into a light, organic phase (11) which is recirculated to the distillation column (6) (process step f)) and a heavy, aqueous phase (12) which is discharged (process step e)). If appropriate, all or part of the stream (12) can be added to the stream (3) or the stream (4). Stream (13) is fractionated in a farther distillation column (14) to give the target product, viz. 1-octene (15), and a 1-methoxyoctane-containing fraction (16) (process step g)).

It is possible to omit the scrub (2) with addition of water (3), and instead use a predecanter for separating off an aqueous phase. FIG. 3 corresponds essentially to FIG. 2 but has been supplemented by the further purification of he 1-octene and the 1-methoxyoctane which may optionally be recirculated. The 1-octene-containing fraction (15) is separated in a distillation column (17) into high-purity 1-octene (19) and a high-boiling fraction (18) (process step h)), where the stream (18) comprises the unwanted octene isomers such as 2-octenes, 3-octenes and 4-octenes and also the nonenes formed as by-product. The 1-methoxyoctane-containing fraction (16) is, to avoid accumulation of high-boiling by-products, separated in a distillation column into 1-methoxyoctane (21) and the high-boiling fraction (22) (process step i)). Stream (21) is advantageously recirculated to the dissociation reaction of process step c).

Figure 2:
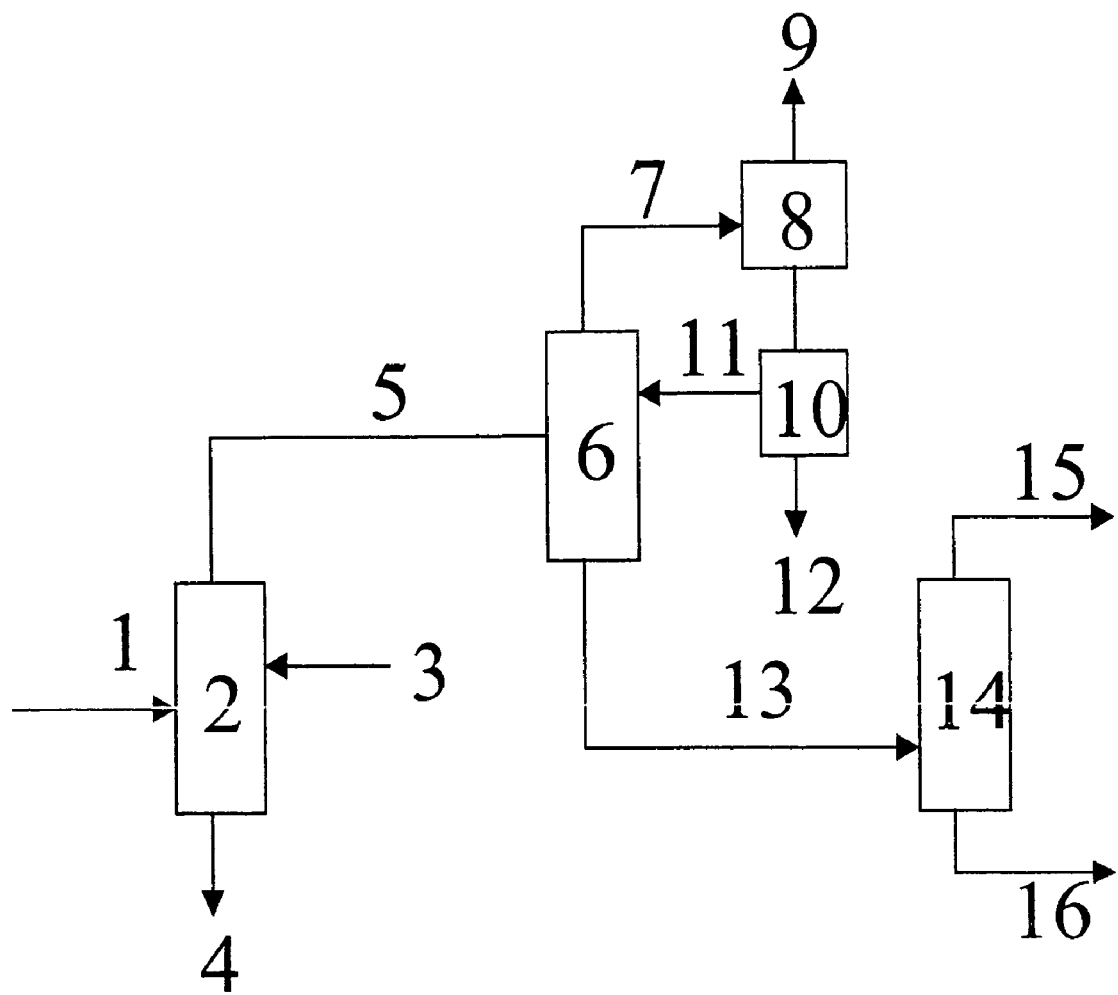
FIG. 2 depicts a multi-step process of preparing 1-octene.
Figure 3:
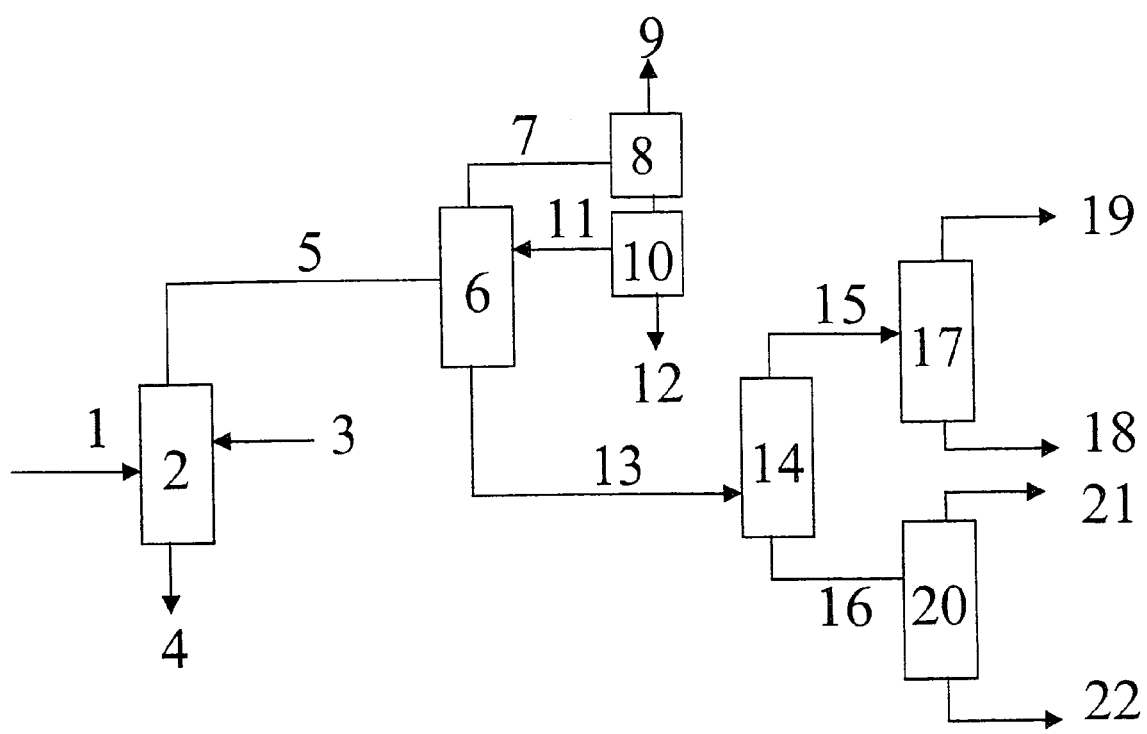
FIG. 3 depicts the process of FIG. 2 supplemented by the further purification of 1-octene and 1-methoxyoctane.
Figure 4:
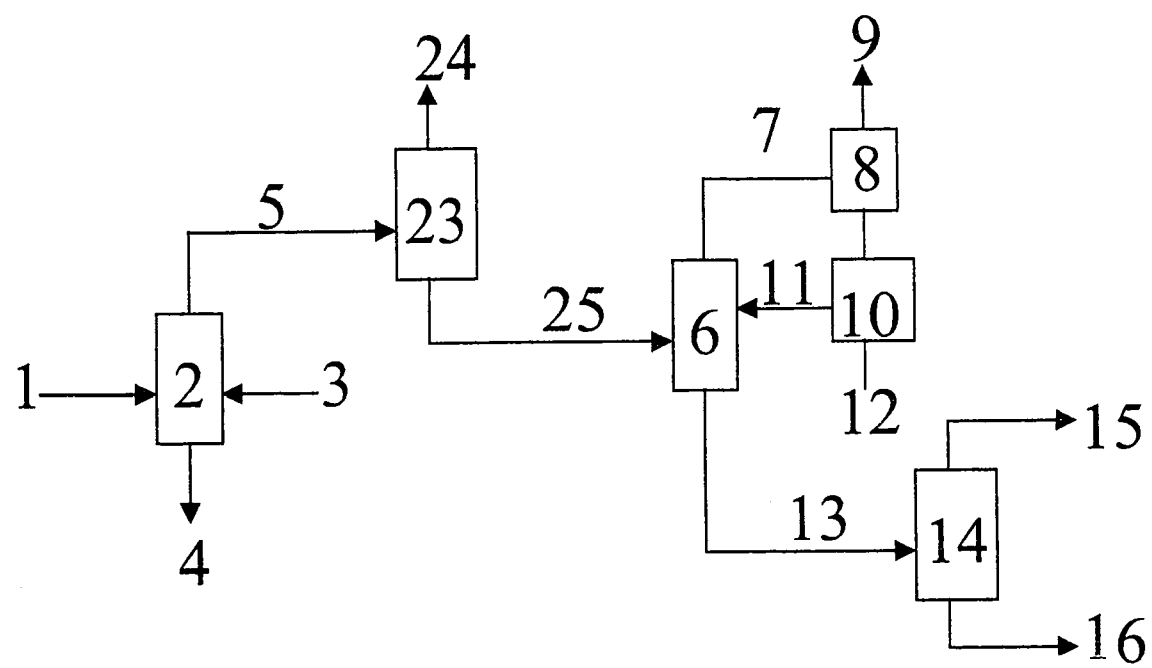
FIG. 4 is a process variant which depicts DME removal and the working-up of high boilers.

In FIG. 4 stream (5) from process step d2) is firstly freed of DME (24) in column (23) (process step d1); the high boilers (25) are worked up either as shown in FIG. 2 or as shown in FIG. 3 (denoted as stream 5). FIG. 4 thus describes a variant of the process of the invention in which the process steps are carried out in the order d2), d1) and d).

Figure 5:
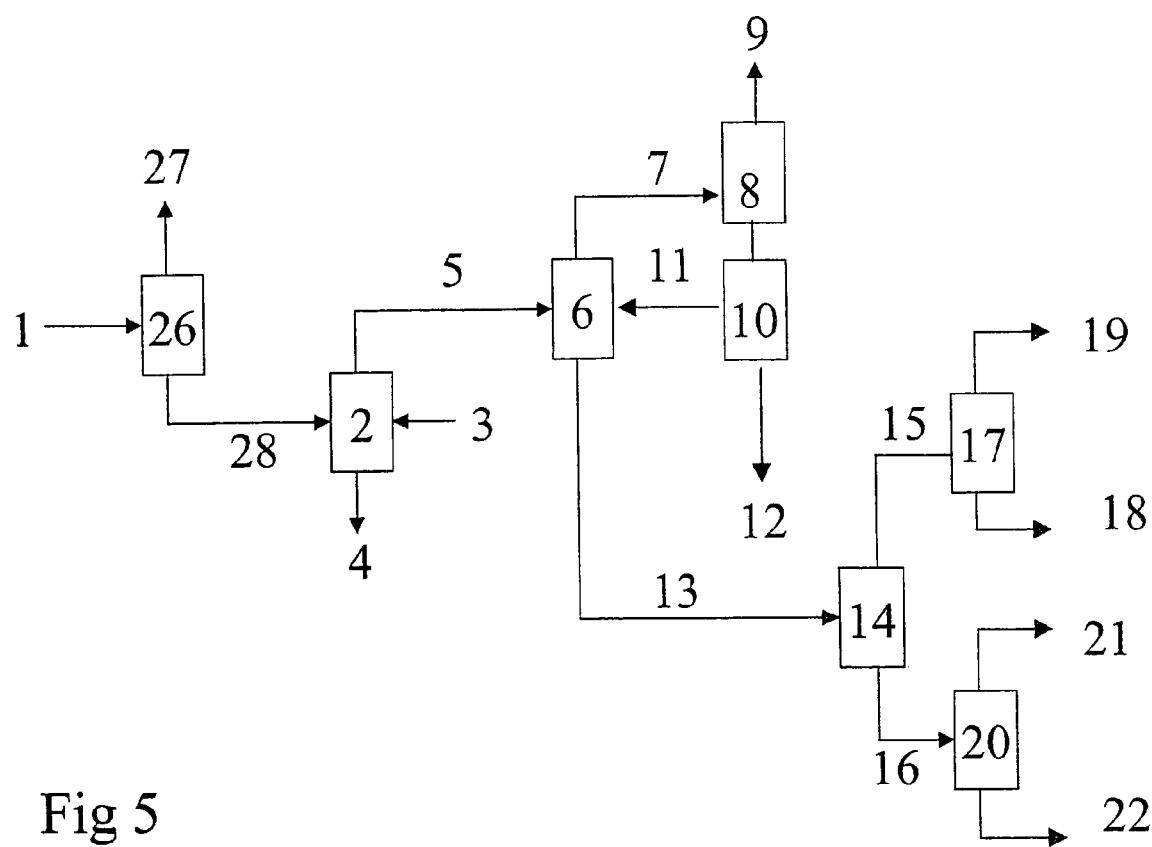
FIG. 5 is another variant in which DME is removed and a bottom stream is processed.

FIG. 5 shows a further variant in which DME (27) is removed in a column (26) (process step d1)) prior to the water scrub (2). The bottom stream (28) obtained in the column (26) is passed to the water scrub (2) (process step d2)) and subsequently worked up as described in FIG. 3. FIG. 5 thus describes a process variant in which the process steps are carried out in the order d1), d2) and d).

Figure 6:
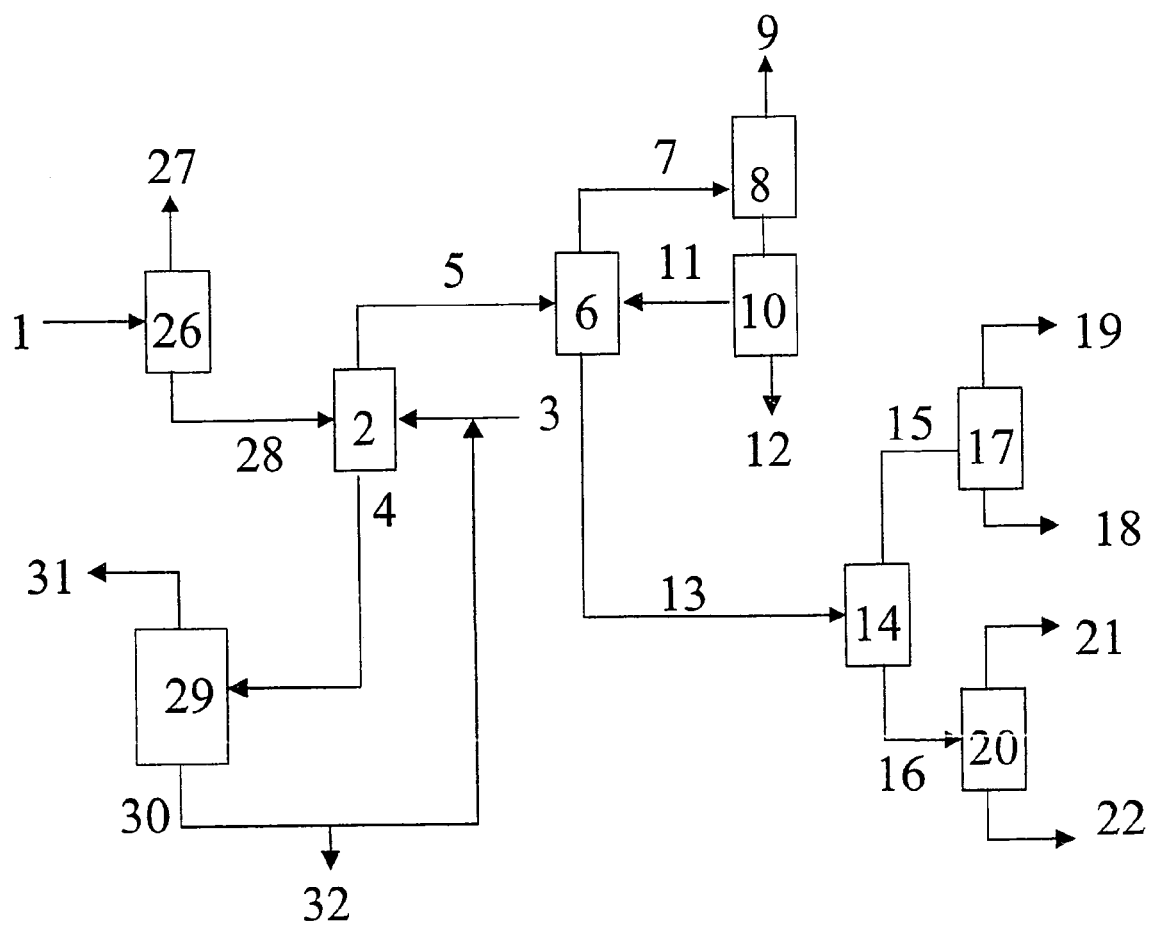
FIG. 6 is a variant of the process of FIG. 5 which is supplemented by a water/methanol work-up.

FIG. 6 shows a variant of FIG. 5 which has been supplemented by a water/methanol work-up (a possible embodiment of process step o)), in which the aqueous solution (4), which may, if appropriate, be combined with stream (12), is separated in a further column (29) into a bottom fraction (30) comprising mainly water and a methanol-containing overhead fraction (31). All or part of the stream (30) can be recirculated as water to the scrubbing step (2). Stream (32) is a purge stream.

Figure 7:
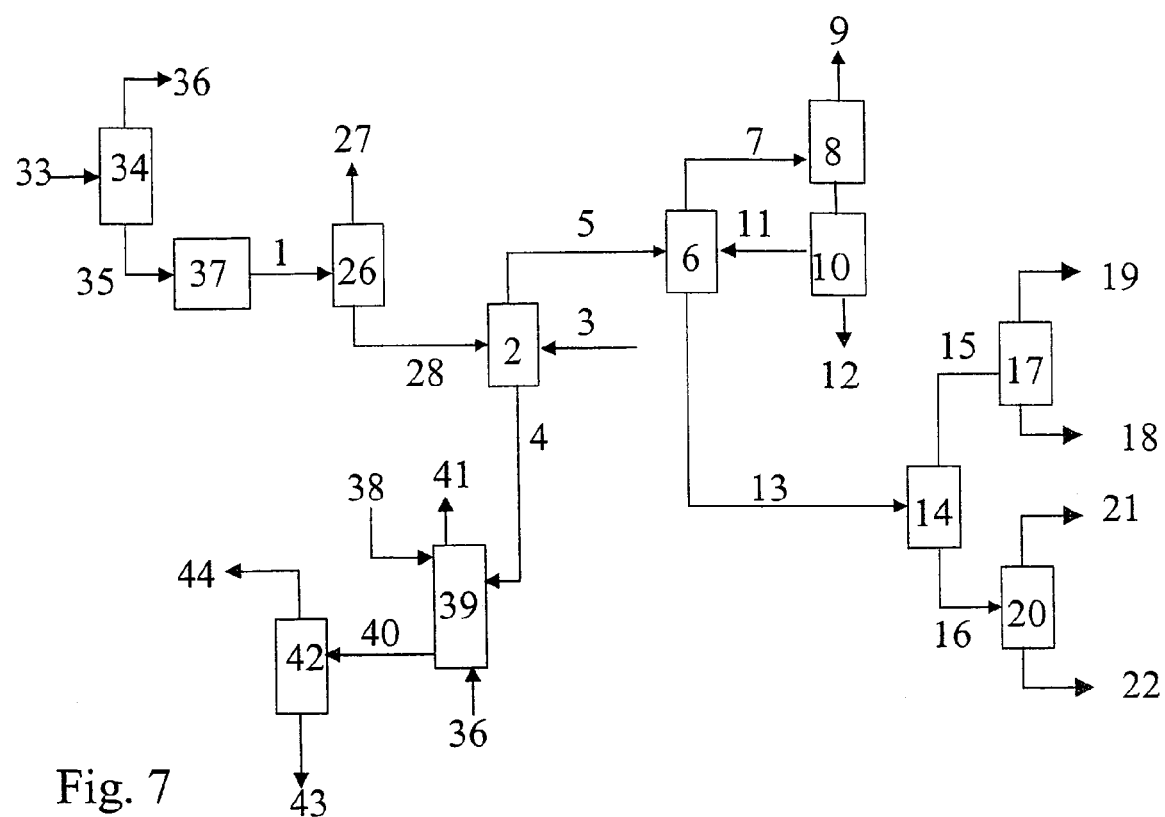
FIG. 7 is a variant of the process of FIG. 5 which is supplemented by a process step in which a methanol containing stream is worked-up.

FIG. 7 shows a further variant of FIG. 5 with a further possible embodiment of process step o), in which a methanol-containing stream from process step 1) is likewise worked up. A product stream from the hydrogenation (stream 33), which comprises 1-methoxyoctane together with methanol, 3-methoxyoctane and $C_8$-hydrocarbons, is separated in a column (34) into a bottom fraction (35) comprising 1-methoxyoctane and an overhead fraction comprising mainly methanol, 3-methoxyoctane and $C_8$-hydrocarbons (36) (process step 1)). Stream (35) is fed to the dissociation (37) from which the dissociation product (1) is obtained. DME (27) is removed from this in column (26). The bottom stream (28) obtained in column (26) is separated in (2) into an organic phase (5) and an aqueous phase (4). If necessary, additional water (3) is added (in engineering terms, this can be configured, for example, as a decanter, mixer-settler or extraction column). The organic phase (5) is worked up as described for FIG. 3. The aqueous phase (4) is conveyed together with stream (36) and, if appropriate, together with stream (12) (not shown) to an extraction (39) into which additional water (38) may be introduced if appropriate. The extraction (39) produces an aqueous phase (40) and an organic phase (41). The aqueous phase (40), which also contains the major part of the methanol, is fed to the column (42) where it is separated into a bottom fraction (43) comprising mainly water and a methanol-containing overhead fraction (44). All or part of the stream (43) can be recirculated as water to step (2) (as stream (3)) or to step (39) (as stream (38)). All or part of the stream (44), which comprises mainly methanol, can be recirculated to the telomerization.

Figure 8:
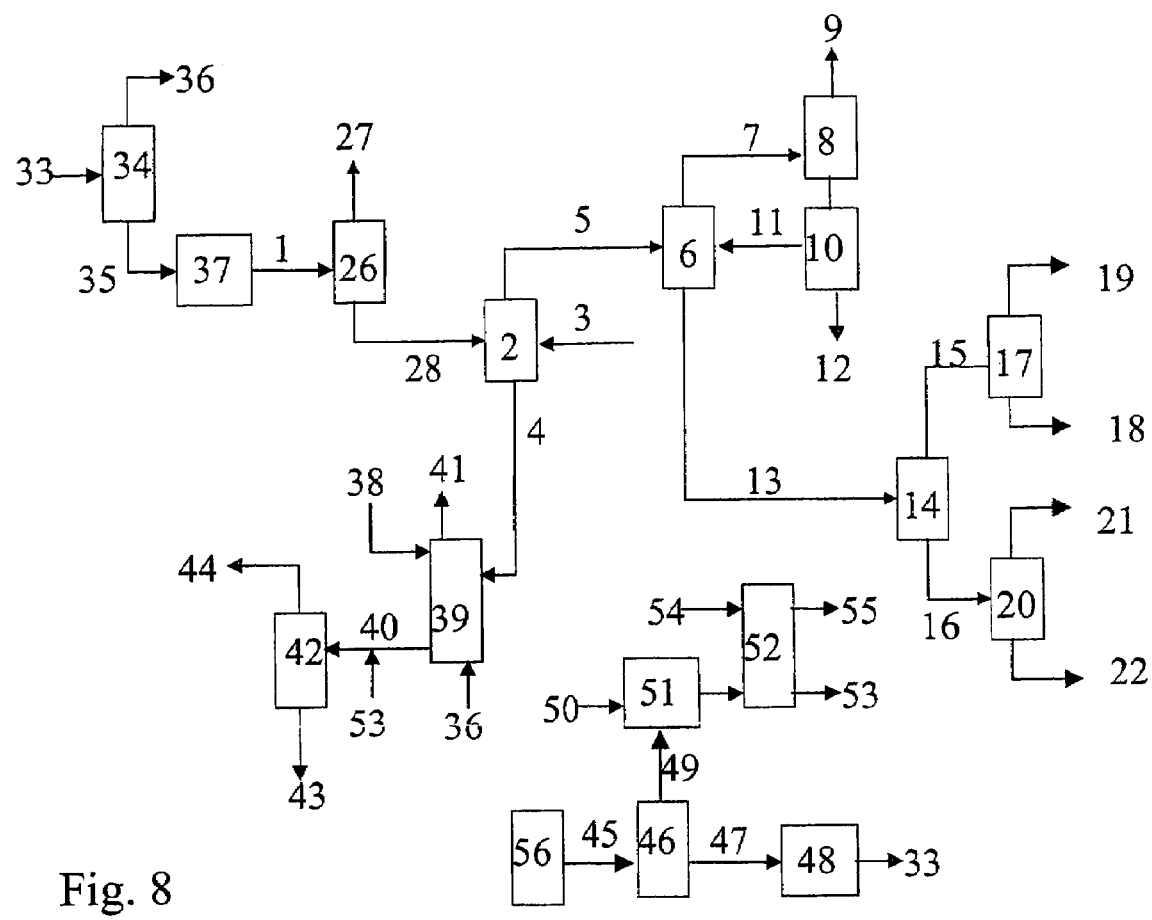
FIG. 8 is a variant of the process of FIG. 7.

FIG. 8 shows an extended variant of FIG. 7. In a separation unit (46) (process step k)), a $C_4$/methanol mixture (49) is separated off from the reaction mixture (45) from the telomerization (56) of the process of the invention and is passed to a selective hydrogenation (51). The remaining stream (47) is fed to the hydrogenation (48) (process step b)) from which the stream (33) is obtained. In the selective hydrogenation (51) (process step m)), residual 1,3-butadiene is reacted with hydrogen (50) to form butenes. The reaction mixture from the selective hydrogenation is passed to a water scrub (52) (process step n)). Here, the methanol present in the $C_4$ is removed by means of water (54). The resulting methanol/water mixture (53) can be purified together with other process streams in column (42). The methanol-free $C_4$ stream (55) has a composition corresponding to commercial raffinate I and is available for other uses. The water (54) used for the extraction can be taken from the stream (43).

To give a clear overview, the main functions of the process steps mentioned in the text under the various embodiments of the process of the invention will once again be listed below.

a) Catalytic reaction of a butadiene-containing stream with methanol to give a stream comprising at least 1-methoxy-2,7-octadiene.

b) Catalytic hydrogenation of the 1-methoxy-2,7-octadiene-containing stream obtained in step a) to give a stream comprising at least 1-methoxyoctane.

c) Catalytic dissociation of at least part of the 1-methoxyoctane to give a dissociation product comprising at least water and 1-octene and possibly unreacted 1-methoxyoctane, d) Separation of the dissociation product from step c) into a gaseous low-boiling fraction comprising at least 1-octene and water and a liquid high-boiling fraction comprising at least 1-octene and 1-methoxyoctane by distillation.

d1) Removal of DME d2) Scrubbing with water to remove methanol.

e) Total or partial condensation of the low-boiling fraction from step d) and separation of the condensate into an aqueous phase and a 1-octene-containing, nonpolar phase.

f) Recirculation of the 1-octene-containing nonpolar phase from step e) to step d).

g) Separation of the high-boiling fraction from d) into a 1-octene-containing fraction and a 1-methoxyoctane-containing fraction.

h) Separation of the 1-octene-containing fraction from g) into a fraction comprising at least 1-octene and a fraction comprising at least $C_8$- and/or $C_9$-olefins.

i) Separation of the 1-methoxyoctane-containing fraction from step g) into a low-boiling fraction comprising at least 1-methoxyoctane and a high-boiling fraction comprising at least dioctyl ether.

k) Part of process step a) in which the unreacted $C_4$-hydrocarbons are separated off. Owing to the formation of azeotropes, this stream still contains some methanol.

l) Purification of the output from step b) by means of a distillation in which the low boilers are separated off from the 1-methoxyoctane.

m) Hydrogenation of residual 1,3-butadiene to butenes.

n) Scrubbing with water to remove methanol from $C_4$-hydrocarbons.

o) Recovery of methanol from aqueous methanol-containing solutions (various embodiments are possible).

The distillation or extraction columns used in the process of the invention are preferably packed columns or have internals such as bubble cap trays, sieve trays or demister packing.

To obtain a satisfactory separation efficiency, the distillation columns should have from 75 to 250 theoretical plates, preferably from 80 to 100 theoretical plates, for the distillation in step h). In the case of the other columns, from 5 to 60 theoretical plates may be sufficient. The column used in process step d) preferably has a reflux ratio of from 0.4 to 0.9. Correspondingly, the reflux ratio of the column in step g) is preferably from 0.6 to 1.4, the column used for the purification of 1-octene in step h) preferably has a reflux ratio of from 4 to 11 and the column in process step i) preferably has a reflux ratio of from 1.9 to 3.7.

The following examples illustrate the present invention without restricting its scope, which is defined by the claims and the description, to these examples.

EXAMPLE 1

A computer model in which the streams and apparatus parameters were dimensioned was set up for the process according to the invention shown in FIG. 5 As simulation software use was made of an AspenPlus simulation model, Version 11.1, from Aspentech. The materials data of the components not present in the Aspen databank were calculated on the basis of the molecular structure using standard methods (the Aspen simulation software). For 1-methoxyoctane, the parameters were refined by fitting to the measured vapor pressure curve. The measurements for determining the vapor pressure curve were carried out in a customary manner.

TABLE 2

Measurements for vapor pressure curve
Vapor pressure of 1-methoxyoctane

| Temperature [° C.] | Pressure [mbar] |
|---|---|
| 52.33 | 9.6 |
| 57.42 | 12.7 |
| 61.06 | 15.5 |
| 65.97 | 20.1 |
| 74.21 | 30.3 |
| 85.08 | 50.4 |
| 92.70 | 70.3 |
| 99.38 | 91.5 |
| 104.12 | 110.5 |
| 112.30 | 150.8 |
| 126.36 | 249.5 |
| 140.45 | 396.1 |
| 153.95 | 595.3 |

TABLE 2-continued

Measurements for vapor pressure curve
Vapor pressure of 1-methoxyoctane

| Temperature [° C.] | Pressure [mbar] |
|---|---|
| 164.21 | 795.3 |
| 173.18 | 1013.9 |

The parameters for the distillation columns are shown in Table 3. The numbering of the columns (block) corresponds to the numbering in FIG. 5.

TABLE 3

Column parameters

| Block | Number of theoretical plates | Pressure at the top bar | Reflux ratio kg/kg |
|---|---|---|---|
| 26 | 20 | 9.0 | 1.0 |
| 6 | 20 | 1.0 | 3.0 |
| 14 | 30 | 1.0 | 1.0 |
| 17 | 100 | 1.0 | 8.0 |
| 20 | 40 | 1.0 | 3.0 |

The streams resulting under these conditions have the compositions listed in Tables 4 a and b. The stream numbers correspond to those in FIG. 5.

TABLE 4a

| | | Stream No. | | | | | | |
|---|---|---|---|---|---|---|---|---|
| | | 1 | 4 | 5 | 9 | 12 | 13 | 15 |
| Mass flow | kg/h | 22500 | 1145 | 19287 | 7 | 320 | 18960 | 13028 |
| Concentrations | | | | | | | | |
| Dimethyl ether | kg/kg | 0.0928 | 0.0006 | 0.0010 | 0.7003 | 0.0462 | 0.0000 | 0.0000 |
| Methanol | kg/kg | 0.0278 | 0.3451 | 0.0119 | 0.1324 | 0.7161 | 0.0000 | 0.0000 |
| Water | kg/kg | 0.0363 | 0.6525 | 0.0036 | 0.0111 | 0.2171 | 0.0000 | 0.0000 |
| Org. low boilers | kg/kg | 0.0004 | 0.0000 | 0.0005 | 0.0754 | 0.0056 | 0.0004 | 0.0005 |
| 1-Octene | kg/kg | 0.5393 | 0.0010 | 0.6291 | 0.0795 | 0.0147 | 0.6397 | 0.9309 |
| 3-/4-Octene | kg/kg | 0.0058 | 0.0000 | 0.0068 | 0.0005 | 0.0001 | 0.0069 | 0.0100 |
| 2-Octene | kg/kg | 0.0222 | 0.0000 | 0.0259 | 0.0008 | 0.0001 | 0.0263 | 0.0383 |
| Nonenes | kg/kg | 0.0109 | 0.0000 | 0.0127 | 0.0000 | 0.0000 | 0.0129 | 0.0187 |
| Cyclooctane | kg/kg | 0.0012 | 0.0000 | 0.0014 | 0.0000 | 0.0000 | 0.0014 | 0.0012 |
| 1-Methoxyoctane | kg/kg | 0.2339 | 0.0002 | 0.2729 | 0.0000 | 0.0000 | 0.2776 | 0.0001 |
| 2-Octanol | kg/kg | 0.0010 | 0.0000 | 0.0012 | 0.0000 | 0.0000 | 0.0012 | 0.0002 |
| 1-Octanol | kg/kg | 0.0171 | 0.0005 | 0.0199 | 0.0000 | 0.0000 | 0.0203 | 0.0000 |
| C16-HCs | kg/kg | 0.0023 | 0.0000 | 0.0027 | 0.0000 | 0.0000 | 0.0027 | 0.0000 |
| Dioctyl ether | kg/kg | 0.0060 | 0.0000 | 0.0070 | 0.0000 | 0.0000 | 0.0071 | 0.0000 |
| High boilers | kg/kg | 0.0030 | 0.0000 | 0.0035 | 0.0000 | 0.0000 | 0.0036 | 0.0000 |

TABLE 4b

| | | Stream No. | | | | | | |
|---|---|---|---|---|---|---|---|---|
| | | 16 | 18 | 19 | 21 | 22 | 27 | 28 |
| Mass flow | kg/h | 5932 | 962 | 12066 | 5419 | 513 | 2068 | 20432 |
| Concentrations | | | | | | | | |
| Dimethyl ether | kg/kg | 0.0000 | 0.0000 | 0.0000 | 0.0000 | 0.0000 | 1.0000 | 0.0010 |
| Methanol | kg/kg | 0.0000 | 0.0000 | 0.0000 | 0.0000 | 0.0000 | 0.0000 | 0.0306 |

TABLE 4b-continued

| | | Stream No. | | | | | | |
|---|---|---|---|---|---|---|---|---|
| | | 16 | 18 | 19 | 21 | 22 | 27 | 28 |
| Water | kg/kg | 0.0000 | 0.0000 | 0.0000 | 0.0000 | 0.0000 | 0.0000 | 0.0400 |
| Org. low boilers | kg/kg | 0.0000 | 0.0000 | 0.0006 | 0.0000 | 0.0000 | 0.0000 | 0.0004 |
| 1-Octene | kg/kg | 0.0000 | 0.2521 | 0.9850 | 0.0000 | 0.0000 | 0.0000 | 0.5939 |
| 3-/4-Octene | kg/kg | 0.0000 | 0.0462 | 0.0071 | 0.0000 | 0.0000 | 0.0000 | 0.0064 |
| 2-Octene | kg/kg | 0.0000 | 0.4273 | 0.0073 | 0.0000 | 0.0000 | 0.0000 | 0.0244 |
| Nonenes | kg/kg | 0.0002 | 0.2534 | 0.0000 | 0.0003 | 0.0000 | 0.0000 | 0.0120 |
| Cyclooctane | kg/kg | 0.0018 | 0.0168 | 0.0000 | 0.0020 | 0.0000 | 0.0000 | 0.0013 |
| 1-Methoxyoctane | kg/kg | 0.8870 | 0.0014 | 0.0000 | 0.9700 | 0.0103 | 0.0000 | 0.2576 |
| 2-Octanol | kg/kg | 0.0033 | 0.0029 | 0.0000 | 0.0036 | 0.0001 | 0.0000 | 0.0011 |
| 1-Octanol | kg/kg | 0.0647 | 0.0001 | 0.0000 | 0.0241 | 0.4941 | 0.0000 | 0.0188 |
| C16-HCs | kg/kg | 0.0087 | 0.0000 | 0.0000 | 0.0000 | 0.1009 | 0.0000 | 0.0025 |
| Dioctyl ether | kg/kg | 0.0228 | 0.0000 | 0.0000 | 0.0000 | 0.2631 | 0.0000 | 0.0066 |
| High boilers | kg/kg | 0.0114 | 0.0000 | 0.0000 | 0.0000 | 0.1306 | 0.0000 | 0.0033 |

EXAMPLE 2 COMPARATIVE EXAMPLE

In Example 2, the simulation model was used to mathematically model the same plant layout as in Example 1 but without overhead decanter (block 10) of the separation unit 6. The column parameters remain unchanged compared to Example 1. The resulting streams have the compositions reported in Tables 5a and 5b.

TABLE 5a

| | | Stream No. | | | | | | |
|---|---|---|---|---|---|---|---|---|
| | | 1 | 4 | 5 | 9 | 12 | 13 | 15 |
| Mass flow | kg/h | 22500 | 1145 | 19287 | 8 | 362 | 18917 | 12985 |
| Concentrations | | | | | | | | |
| Dimethyl ether | kg/kg | 0.0928 | 0.0006 | 0.0010 | 0.5235 | 0.0429 | 0.0000 | 0.0000 |
| Methanol | kg/kg | 0.0278 | 0.3451 | 0.0119 | 0.3159 | 0.6251 | 0.0001 | 0.0001 |
| Water | kg/kg | 0.0363 | 0.6525 | 0.0036 | 0.0025 | 0.0065 | 0.0036 | 0.0052 |
| Org. low boilers | kg/kg | 0.0004 | 0.0000 | 0.0005 | 0.0044 | 0.0020 | 0.0004 | 0.0006 |
| 1-Octene | kg/kg | 0.5393 | 0.0010 | 0.6291 | 0.1486 | 0.3122 | 0.6353 | 0.9256 |
| 3-/4-Octene | kg/kg | 0.0058 | 0.0000 | 0.0068 | 0.0014 | 0.0030 | 0.0068 | 0.0100 |
| 2-Octene | kg/kg | 0.0222 | 0.0000 | 0.0259 | 0.0037 | 0.0084 | 0.0262 | 0.0382 |
| Nonenes | kg/kg | 0.0109 | 0.0000 | 0.0127 | 0.0000 | 0.0000 | 0.0130 | 0.0188 |
| Cyclooctane | kg/kg | 0.0012 | 0.0000 | 0.0014 | 0.0000 | 0.0000 | 0.0014 | 0.0012 |
| 1-Methoxyoctane | kg/kg | 0.2339 | 0.0002 | 0.2729 | 0.0000 | 0.0000 | 0.2782 | 0.0001 |
| 2-Octanol | kg/kg | 0.0010 | 0.0000 | 0.0012 | 0.0000 | 0.0000 | 0.0012 | 0.0002 |
| 1-Octanol | kg/kg | 0.0171 | 0.0005 | 0.0199 | 0.0000 | 0.0000 | 0.0203 | 0.0000 |
| C16-HCs | kg/kg | 0.0023 | 0.0000 | 0.0027 | 0.0000 | 0.0000 | 0.0027 | 0.0000 |
| Dioctyl ether | kg/kg | 0.0060 | 0.0000 | 0.0070 | 0.0000 | 0.0000 | 0.0071 | 0.0000 |
| High boilers | kg/kg | 0.0030 | 0.0000 | 0.0035 | 0.0000 | 0.0000 | 0.0036 | 0.0000 |

TABLE 5b

| | | Stream No. | | | | | | |
|---|---|---|---|---|---|---|---|---|
| | | 16 | 18 | 19 | 21 | 22 | 27 | 28 |
| Mass flow | kg/h | 5932 | 1028 | 11958 | 5419 | 513 | 2068 | 20432 |
| Concentrations | | | | | | | | |
| Dimethyl ether | kg/kg | 0.0000 | 0.0000 | 0.0000 | 0.0000 | 0.0000 | 1.0000 | 0.0010 |
| Methanol | kg/kg | 0.0000 | 0.0000 | 0.0001 | 0.0000 | 0.0000 | 0.0000 | 0.0306 |
| Water | kg/kg | 0.0000 | 0.0000 | 0.0000 | 0.0000 | 0.0000 | 0.0000 | 0.0400 |
| Org. low boilers | kg/kg | 0.0000 | 0.0000 | 0.0007 | 0.0000 | 0.0000 | 0.0000 | 0.0004 |
| 1-Octene | kg/kg | 0.0000 | 0.2339 | 0.9850 | 0.0000 | 0.0000 | 0.0000 | 0.5939 |
| 3-/4-Octene | kg/kg | 0.0000 | 0.0571 | 0.0059 | 0.0000 | 0.0000 | 0.0000 | 0.0064 |
| 2-Octene | kg/kg | 0.0000 | 0.4523 | 0.0027 | 0.0000 | 0.0000 | 0.0000 | 0.0244 |
| Nonenes | kg/kg | 0.0002 | 0.2372 | 0.0000 | 0.0003 | 0.0000 | 0.0000 | 0.0120 |
| Cyclooctane | kg/kg | 0.0019 | 0.0155 | 0.0000 | 0.0020 | 0.0000 | 0.0000 | 0.0013 |
| 1-Methoxyoctane | kg/kg | 0.8869 | 0.0013 | 0.0000 | 0.9700 | 0.0102 | 0.0000 | 0.2576 |
| 2-Octanol | kg/kg | 0.0033 | 0.0026 | 0.0000 | 0.0037 | 0.0001 | 0.0000 | 0.0011 |
| 1-Octanol | kg/kg | 0.0647 | 0.0001 | 0.0000 | 0.0240 | 0.4944 | 0.0000 | 0.0188 |
| C16-HCs | kg/kg | 0.0087 | 0.0000 | 0.0000 | 0.0000 | 0.1008 | 0.0000 | 0.0025 |
| Dioctyl ether | kg/kg | 0.0228 | 0.0000 | 0.0000 | 0.0000 | 0.2630 | 0.0000 | 0.0066 |
| High boilers | kg/kg | 0.0114 | 0.0000 | 0.0000 | 0.0000 | 0.1315 | 0.0000 | 0.0033 |

It can be seen that the absence of the overhead decanter leads to losses of the 1-octene product in the stream 12. About 1% of the 1-octene is lost here. In addition, the final 1-octene product formally contains about 5600 ppm of residual water which would have to be removed in additional steps. In contrast, the process design according to the invention enables both methanol and water to be removed from the 1-octene product in accordance with specifications.

EXAMPLE 3

A computer model in which the streams and apparatus parameters were dimensioned was set up for the process according to the invention shown in FIG. 7. The simulation software and the materials data correspond to those in Example 1.

The parameters for the distillation columns are shown in Table 6. The numbering of the columns (block) corresponds to the numbering in FIG. 7. Block (39) is an extraction column.

TABLE 6

Column parameters

| Block | Number of theoretical plates | Pressure at the top bar | Reflux ratio kg/kg |
|---|---|---|---|
| 34 | 50 | 1.0 | 2.0 |
| 26 | 20 | 9.0 | 1.0 |
| 6 | 20 | 1.0 | 3.0 |
| 14 | 30 | 1.0 | 1.0 |
| 17 | 100 | 1.0 | 8.0 |
| 20 | 40 | 1.0 | 3.0 |
| 39 | 5 | 1.0 | — |
| 42 | 30 | 1.0 | 2.0 |

The streams resulting under these conditions have the compositions listed in Tables 7a, b and c. The stream numbers correspond to those in FIG. 7.

TABLE 7a

| | Stream No. | | | | | | | |
|---|---|---|---|---|---|---|---|---|
| | 1 | 4 | 5 | 9 | 12 | 13 | 15 | 16 |
| Mass flow in kg/h | 22500 | 1145 | 19287 | 7 | 320 | 18960 | 13028 | 5932 |
| Concentrations in kg/kg | | | | | | | | |
| C4-HCs | 0.0000 | 0.0000 | 0.0000 | 0.0000 | 0.0000 | 0.0000 | 0.0000 | 0.0000 |
| Dimethyl ether | 0.0928 | 0.0006 | 0.0010 | 0.7003 | 0.0462 | 0.0000 | 0.0000 | 0.0000 |
| Methanol | 0.0278 | 0.3451 | 0.0119 | 0.1324 | 0.7161 | 0.0000 | 0.0000 | 0.0000 |
| Water | 0.0363 | 0.6525 | 0.0036 | 0.0111 | 0.2171 | 0.0000 | 0.0000 | 0.0000 |
| Org. low boilers | 0.0004 | 0.0000 | 0.0005 | 0.0754 | 0.0056 | 0.0004 | 0.0005 | 0.0000 |
| 1-Octene | 0.5393 | 0.0010 | 0.6291 | 0.0795 | 0.0147 | 0.6397 | 0.9309 | 0.0000 |
| 3-/4-Octene | 0.0058 | 0.0000 | 0.0068 | 0.0005 | 0.0001 | 0.0069 | 0.0100 | 0.0000 |
| 2-Octene | 0.0222 | 0.0000 | 0.0259 | 0.0008 | 0.0001 | 0.0263 | 0.0383 | 0.0000 |
| n-Octane | 0.0001 | 0.0000 | 0.0001 | 0.0000 | 0.0000 | 0.0001 | 0.0002 | 0.0000 |
| Nonenes | 0.0108 | 0.0000 | 0.0126 | 0.0000 | 0.0000 | 0.0128 | 0.0185 | 0.0002 |
| Cyclooctane | 0.0012 | 0.0000 | 0.0014 | 0.0000 | 0.0000 | 0.0014 | 0.0012 | 0.0018 |
| 3-Methoxyoctane | 0.0000 | 0.0000 | 0.0000 | 0.0000 | 0.0000 | 0.0000 | 0.0000 | 0.0000 |
| 1-Methoxyoctane | 0.2339 | 0.0002 | 0.2729 | 0.0000 | 0.0000 | 0.2776 | 0.0001 | 0.8870 |
| 2-Octanol | 0.0010 | 0.0000 | 0.0012 | 0.0000 | 0.0000 | 0.0012 | 0.0002 | 0.0033 |
| 1-Octanol | 0.0171 | 0.0005 | 0.0199 | 0.0000 | 0.0000 | 0.0203 | 0.0000 | 0.0647 |
| C16-HCs | 0.0023 | 0.0000 | 0.0027 | 0.0000 | 0.0000 | 0.0027 | 0.0000 | 0.0087 |
| Dioctyl ether | 0.0060 | 0.0000 | 0.0070 | 0.0000 | 0.0000 | 0.0071 | 0.0000 | 0.0228 |
| High boilers | 0.0030 | 0.0000 | 0.0035 | 0.0000 | 0.0000 | 0.0036 | 0.0000 | 0.0114 |

TABLE 7b

| | Stream No. | | | | | | | |
|---|---|---|---|---|---|---|---|---|
| | 18 | 19 | 21 | 22 | 27 | 28 | 33 | 35 |
| Mass flow in kg/h | 962 | 12066 | 5419 | 513 | 2068 | 20432 | 29346 | 22503 |
| Concentrations in kg/kg | | | | | | | | |
| C4-HCs | 0.0000 | 0.0000 | 0.0000 | 0.0000 | 0.0000 | 0.0000 | 0.0001 | 0.0000 |
| Dimethyl ether | 0.0000 | 0.0000 | 0.0000 | 0.0000 | 1.0000 | 0.0010 | 0.0000 | 0.0000 |
| Methanol | 0.0000 | 0.0000 | 0.0000 | 0.0000 | 0.0000 | 0.0306 | 0.2079 | 0.0000 |
| Water | 0.0000 | 0.0000 | 0.0000 | 0.0000 | 0.0000 | 0.0400 | 0.0000 | 0.0000 |
| Org. low boilers | 0.0000 | 0.0006 | 0.0000 | 0.0000 | 0.0000 | 0.0004 | 0.0000 | 0.0000 |
| 1-Octene | 0.2521 | 0.9850 | 0.0000 | 0.0000 | 0.0000 | 0.5939 | 0.0000 | 0.0000 |
| 3-/4-Octene | 0.0462 | 0.0071 | 0.0000 | 0.0000 | 0.0000 | 0.0064 | 0.0000 | 0.0000 |
| 2-Octene | 0.4273 | 0.0073 | 0.0000 | 0.0000 | 0.0000 | 0.0244 | 0.0000 | 0.0000 |
| n-Octane | 0.0023 | 0.0000 | 0.0000 | 0.0000 | 0.0000 | 0.0001 | 0.0057 | 0.0000 |
| Nonenes | 0.2510 | 0.0000 | 0.0003 | 0.0000 | 0.0000 | 0.0119 | 0.0000 | 0.0000 |
| Cyclooctane | 0.0168 | 0.0000 | 0.0020 | 0.0000 | 0.0000 | 0.0013 | 0.0000 | 0.0000 |
| 3-Methoxyoctane | 0.0000 | 0.0000 | 0.0000 | 0.0000 | 0.0000 | 0.0000 | 0.0161 | 0.0010 |
| 1-Methoxyoctane | 0.0014 | 0.0000 | 0.9700 | 0.0103 | 0.0000 | 0.2576 | 0.7702 | 0.9990 |
| 2-Octanol | 0.0029 | 0.0000 | 0.0036 | 0.0001 | 0.0000 | 0.0011 | 0.0000 | 0.0000 |
| 1-Octanol | 0.0001 | 0.0000 | 0.0241 | 0.4941 | 0.0000 | 0.0188 | 0.0000 | 0.0000 |

TABLE 7b-continued

| | Stream No. | | | | | | | |
|---|---|---|---|---|---|---|---|---|
| | 18 | 19 | 21 | 22 | 27 | 28 | 33 | 35 |
| C16-HCs | 0.0000 | 0.0000 | 0.0000 | 0.1009 | 0.0000 | 0.0025 | 0.0000 | 0.0000 |
| Dioctyl ether | 0.0000 | 0.0000 | 0.0000 | 0.2631 | 0.0000 | 0.0066 | 0.0000 | 0.0000 |
| High boilers | 0.0000 | 0.0000 | 0.0000 | 0.1316 | 0.0000 | 0.0033 | 0.0000 | 0.0000 |

TABLE 7c

| | Stream No. | | | | | |
|---|---|---|---|---|---|---|
| | 36 | 38 | 40 | 41 | 43 | 44 |
| Mass flow in kg/h | 6842 | 13000 | 20241 | 746 | 13778 | 6463 |
| Concentrations in kg/kg | | | | | | |
| C4-HCs | 0.0004 | 0.0000 | 0.0001 | 0.0019 | 0.0000 | 0.0002 |
| Dimethyl ether | 0.0000 | 0.0000 | 0.0000 | 0.0001 | 0.0000 | 0.0001 |
| Methanol | 0.8915 | 0.0470 | 0.3509 | 0.0029 | 0.0469 | 0.9990 |
| Water | 0.0000 | 0.9521 | 0.6483 | 0.0039 | 0.9524 | 0.0000 |
| Org. low boilers | 0.0000 | 0.0000 | 0.0000 | 0.0000 | 0.0000 | 0.0000 |
| 1-Octene | 0.0000 | 0.0000 | 0.0000 | 0.0016 | 0.0000 | 0.0000 |
| 3-/4-Octene | 0.0000 | 0.0000 | 0.0000 | 0.0000 | 0.0000 | 0.0000 |
| 2-Octene | 0.0000 | 0.0000 | 0.0000 | 0.0001 | 0.0000 | 0.0000 |
| n-Octane | 0.0243 | 0.0000 | 0.0002 | 0.2174 | 0.0000 | 0.0006 |
| Nonenes | 0.0000 | 0.0000 | 0.0000 | 0.0000 | 0.0000 | 0.0000 |
| Cyclooctane | 0.0000 | 0.0000 | 0.0000 | 0.0000 | 0.0000 | 0.0000 |
| 3-Methoxyoctane | 0.0659 | 0.0007 | 0.0004 | 0.6060 | 0.0005 | 0.0000 |
| 1-Methoxyoctane | 0.0179 | 0.0002 | 0.0001 | 0.1653 | 0.0001 | 0.0000 |
| 2-Octanol | 0.0000 | 0.0000 | 0.0000 | 0.0000 | 0.0000 | 0.0000 |
| 1-Octanol | 0.0000 | 0.0000 | 0.0000 | 0.0008 | 0.0000 | 0.0000 |
| C16-HCs | 0.0000 | 0.0000 | 0.0000 | 0.0000 | 0.0000 | 0.0000 |
| Dioctyl ether | 0.0000 | 0.0000 | 0.0000 | 0.0000 | 0.0000 | 0.0000 |
| High boilers | 0.0000 | 0.0000 | 0.0000 | 0.0000 | 0.0000 | 0.0000 |

Dealing with the methanol-containing streams (4) and (36) together in a joint work-up enables organic compounds to be separated off via a simple extraction column. The methanol can then be recovered in a purity of 99.9% from the methanol-containing aqueous solution (40).

The invention claimed is:

1. Process for preparing 1-octene comprising:
   a) reacting catalytically a butadiene-containing stream with methanol to give a stream comprising at least 1-methoxy-2,7-octadiene,
   b) hydrogenating catalytically the 1-methoxy-2,7-octadiene-containing stream to give a stream comprising at least 1-methoxyoctane, and
   c) dissociating catalytically at least part of the 1-methoxyoctane to give a dissociation product comprising at least water and 1-octene,
   wherein
   d) the dissociation product from c) is separated by distillation into a gaseous low-boiling fraction comprising at least 1-octene and water and a liquid high-boiling fraction comprising at least 1-octene and 1-methoxyoctane,
   e) the low-boiling fraction is completely or partially condensed and separated into an aqueous phase and a 1-octene-containing, nonpolar phase,
   f) the nonpolar phase from e) is recirculated to step d) and
   g) the high-boiling fraction from d) is separated into a 1-octene-containing fraction and a 1-methoxyoctane-containing fraction.

2. The process as claimed in claim 1, wherein d1) the dissociation product from c) comprises dimethyl ether (DME) and is separated by distillation into a low-boiling fraction comprising at least DME and a high-boiling fraction which is at least partly passed to step d).

3. The process as claimed in claim 2, wherein the high-boiling fraction from d1) comprises methanol and is washed with water to give a methanol-containing aqueous stream and a nonpolar stream which is passed to step d).

4. The process as claimed in claim 1, wherein d2) comprises methanol as dissociation product from c) and is washed with water to give a methanol-containing, aqueous stream and a nonpolar stream which is passed at least partly to step d).

5. The process as claimed in claim 4, wherein the nonpolar stream comprises at least DME and is separated by distillation into a low-boiling fraction comprising at least DME and a high-boiling fraction which is passed to step d).

6. The process as claimed in claim 1, wherein the 1-octene-containing fraction from g) is separated in a step h) into a fraction comprising at least 1-octene and a fraction comprising at least $C_8$- and $C_9$-olefins.

7. The process as claimed in claim 1, wherein the 1-methoxyoctane-containing fraction from g) is separated in a step i) into a low-boiling fraction comprising 1-methoxyoctane and a high-boiling fraction comprising at least dioctyl ether.

8. The process as claimed in claim 7, wherein the low-boiling fraction is recirculated to step c).

9. The process as claimed in claim 1, wherein k) the step a) comprises, after the catalytic reaction, a distillation step in which the $C_4$-hydrocarbons are separated off by distillation and the remaining stream which has a $C_4$-hydrocarbon content of less than 5% by weight is passed to step b).

10. The process as claimed in claim 1, wherein l) the stream from step b) is separated by distillation into a low-boiling fraction comprising at least methanol, 3-methoxyoctane and $C_8$-hydrocarbons and a low-boiling fraction comprising at least 1-methoxyoctane and the high-boiling fraction is passed to step c).

11. The process as claimed in claim 3, wherein the methanol and/or the water is/are separated off from the aqueous, methanol-containing stream in a step o).

12. The process as claimed in claim 11, wherein the aqueous phase from step e) is likewise fed to step o).

13. The process as claimed in claim 11, wherein the low-boiling fraction from step e) is likewise fed to step o).

14. The process as claimed in claim 11, wherein an organic phase is separated off from the stream in step o) and the aqueous phase is separated by distillation into a low-boiling fraction comprising methanol and a high-boiling fraction comprising water.

15. The process as claimed in claim 14, wherein the organic phase is separated off by extraction.

16. The process as claimed in claim 11, wherein all or part of the methanol is recirculated to step a) (telomerization).

* * * * *